(12) United States Patent
Raymondos (10) Patent No.: US 9,662,068 B2
(45) Date of Patent: May 30, 2017

(54) MEDICAL DEVICE FOR CONDUCTING A MEDICAL EXAMINATION AND/OR INTERVENTION

(75) Inventor: Konstantinos Raymondos, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 372 days.

(21) Appl. No.: 13/981,941

(22) PCT Filed: Jan. 27, 2012

(86) PCT No.: PCT/EP2012/051324
§ 371 (c)(1),
(2), (4) Date: Oct. 9, 2013

(87) PCT Pub. No.: WO2012/101254
PCT Pub. Date: Aug. 2, 2012

(65) Prior Publication Data
US 2014/0039255 A1 Feb. 6, 2014

(30) Foreign Application Priority Data
Jan. 27, 2011 (EP) .................................... 11152409

(51) Int. Cl.
*A61B 1/00* (2006.01)
*A61B 5/00* (2006.01)
(Continued)

(52) U.S. Cl.
CPC ............ *A61B 5/6826* (2013.01); *A61B 1/008* (2013.01); *A61B 1/00016* (2013.01);
(Continued)

(58) Field of Classification Search
CPC . A61B 1/00147; A61B 1/00149; A61B 1/267; A61B 1/00052; A61B 1/00098; A61B 1/008; A61B 1/05; A61B 1/07
(Continued)

(56) References Cited

U.S. PATENT DOCUMENTS 4,337,761 A * 7/1982 Upsher .................... A61B 1/07
600/188
4,991,592 A 2/1991 Christ
(Continued)

FOREIGN PATENT DOCUMENTS

WO 96/27991 A1 9/1996
WO 2005/107832 A1 11/2005

*Primary Examiner* — Timothy J Neal
(74) *Attorney, Agent, or Firm* — Whitham, Curtis & Cook, P.C.

(57) ABSTRACT

The invention is related to a medical device for conducting a medical examination and/or intervention within a human or animal body the medical device (1) comprising an elongate body (2) which is designed for introduction into an orifice (15) of the human or animal body the elongate body (2) comprising a distal end (3), which is on the front side of the elongate body during introduction into the orifice (15), of the human or animal body and a proximal end (4) on the opposite side, wherein the elongate body is a hollow body comprising a reception chamber (8) in its interior, which reception chamber (8) is arranged for reception of a human finger (9), characterized in that one or more guiding elements (5, 21) for guiding a medical examination and/or intervention component (6) are located on or in the elongate body and at least one image gathering device (7), which is arranged for gathering of images in front of the distal end (3) of the elongate body (2), is arranged on or in the elongate body (2).

16 Claims, 6 Drawing Sheets

(51) Int. Cl.
*A61B 1/018* (2006.01)
*A61B 1/05* (2006.01)
*A61B 1/267* (2006.01)
*A61B 1/008* (2006.01)
*A61B 1/07* (2006.01)
*A61B 1/12* (2006.01)
*A61B 1/303* (2006.01)
*A61M 16/04* (2006.01)

(52) U.S. Cl.
CPC ...... *A61B 1/00045* (2013.01); *A61B 1/00094* (2013.01); *A61B 1/00098* (2013.01); *A61B 1/018* (2013.01); *A61B 1/05* (2013.01); *A61B 1/07* (2013.01); *A61B 1/126* (2013.01); *A61B 1/267* (2013.01); *A61B 1/303* (2013.01); *A61M 16/0488* (2013.01)

(58) Field of Classification Search
USPC ........ 600/102, 114, 139, 141, 156, 157, 104
See application file for complete search history.

(56) References Cited

U.S. PATENT DOCUMENTS

| | | | |
|---|---|---|---|
| 5,079,629 A | 1/1992 | Oz | |
| 5,386,817 A * | 2/1995 | Jones | 600/104 |
| 2006/0173244 A1* | 8/2006 | Boulais et al. | 600/156 |
| 2007/0270646 A1* | 11/2007 | Weiner | 600/121 |
| 2008/0064928 A1* | 3/2008 | Otawara | 600/129 |
| 2009/0222967 A1* | 9/2009 | Winningham et al. | 2/21 |

* cited by examiner

MEDICAL DEVICE FOR CONDUCTING A MEDICAL EXAMINATION AND/OR INTERVENTION

The invention is related to a medical device for conducting a medical examination and/or intervention within a human or animal body according to claim 1. The medical device can be used for conducting e.g. a laryngoscopy, an intubation and/or any other medical examination and/or intervention within a human or animal body, like in the area of gynaecology or for a biopsy.

In the area of laryngoscopy and endo-tracheal intubation several difficulties can occur, in particular in case of challenging airways, like airways with anatomical anomalies, e.g. airways which are small in diameter and/or comprise curved portions which require high bending angles for an oral-tracheal tube, or airways with pathological changes like tumors. Even in cases with normal airways problems can occur, in particular in emergency situations or due to lack of experience.

A laryngoscopy is a medical method of examination of the larynx. An intubation is an insertion of a tube, in particular an oral-tracheal tube, through an oral airway into the trachea. An intubation normally requires a device for laryngoscopy, for example the so-called laryngoscope. Such a laryngoscope normally includes guiding elements for guiding the tube.

Known medical devices are described e.g. in U.S. Pat. No. 6,843,769 B1 or U.S. Pat. No. 7,156,091 B2.

It is an object of the present invention to provide a medical device which allows for conducting a laryngoscopy and/or an intubation in an easier and safer manner, both for normal and for challenging airways. It is a further object of the present invention to provide a medical device which is also suitable for conducting other types of medical examination and/or invention within a human or animal body.

This object is achieved by a medical device according to claim 1. This has the advantage that a tactile controlled medical examination and/or intervention of any kind within a human or animal body can be conducted, like e.g. a laryngoscopy and/or intubation, which is controlled by a human finger, e.g. by the forefinger of a user. The medical device can be slipped over the human finger. Then a laryngoscopy or intubation can be conducted without further supporting equipment. Because of the tactile or haptic feedback provided to the finger, it is much easier to find the way into the trachea of a person than with conventional devices. This allows a significant faster and safer intubation process. The medical device can be manufactured very small so that the distal end of the medical device can be guided by the finger directly to vocal cords, which allows for a precise finger-guided intubation. This allows in particular for an easy and safe intubation of persons having a minimum diameter of the oral areas of less than 2.5 cm.

As already mentioned, the medical device can be used also for other types of medical examinations and/or interventions like surgical procedures or for a biopsy. For example, the medical device can be used for tactile examinations in the area of gynaecology or proctology. While the medical device has a broad range of possible uses, in the following description the aspects of using the medical device in the area of laryngoscopy and/or intubation are mainly described.

Advantageously the medical device is flexibly guidable by means of movement of the finger. Mainly the distal phalanx of the finger allows for a precise guiding and movement of the medical device during insertion into the larynx. The medical device can be slipped over the human finger from the proximal end of the elongate body which comprises an opening for insertion of the finger.

The medical device can be made with fixed dimensions of the reception chamber, for example with fixed inner cross-sectional area and fixed length. In this case, a variety of medical devices having different length and inner cross-sectional areas shall be provided for different finger sizes of possible users. It is also advantageous to manufacture the medical device in a way that the inner cross-sectional area and/or the length of the reception chamber is variably adaptable to the human finger, e.g. by making the length and/or the inner cross-sectional area adjustable. Several technologies are applicable for achieving such adjustability, e.g. through hook and loop tape fixed to parts of the elongate body, or by using bendable metal material for adapting and fixing the medical device to the human finger. The elongate body can be a one-piece or multiple-piece element. It can comprise a zip-fastener mounted along the elongate body, which allows for easy slipping of the medical device over the human finger and then fastening the medical device on the finger by closing the zip-fastener.

A further advantage is that a stiletto used in conventional FTV-laryngoscopy (free-guided tube placement videolaryngoscopy) can be avoided, which further increases the safety of the patient.

The elongate body as well as the reception chamber can be manufactured as closed elements only providing the necessary openings for the finger and, in case it is designed for intubation, for an oral-tracheal tube. It is also possible to manufacture the elongate body as well as the reception chamber with openings, e.g. for venting the finger or for reducing the weight of the medical device. The elongate body can be made with our without several openings, e.g. like a lattice, a mesh or a fabric.

Generally, the medical device can be made of a material which provides sufficient elasticity to allow the required movement through movement of the finger. The medical device can be manufactured in several ways, for example as a one-way device made of low-priced materials or as a more robust and endurable device made of more endurable materials. Materials for the medical device can include all kinds of metals, plastic materials, rubber or other elastic materials.

According to the invention, one or more guiding elements for guiding a medical examination and/or intervention component, like e.g. a tube or a biopsy needle, are located on or in the elongate body. The one or more guiding elements can be arranged for guiding the medical examination and/or intervention component along the medical device. According to the invention, at least one image gathering device, which is arranged for gathering of images in the area of the distal end of the elongate body, is arranged on or in the elongate body. In particular, the tube can be an oral-tracheal tube or a specific suction tube for removing larger size debris particles. In particular, the image gathering device can be arranged for gathering of images in the front of the distal end of the elongate body.

The medical examination and/or intervention component which can be guided through the guiding elements along the medical device can be, in case of use of the medical device in the area of gynaecology, a device for conducting a smear test of the cervix, like a stick or a spatula with absorbent cotton. Advantageously the inventive medical device allows for an optical examination as well as for conducting the smear test within the same step, since the medical device comprises both the image gathering device and the guiding elements for guiding the medical examination and/or intervention component. Thus, the time and effort for conducting the gynaecological examination is reduced, thereby reducing inconveniences for the patient. In a similar manner the medical device can be used for proctological examinations.

According to an advantageous embodiment of the invention, the inner cross-sectional area and/or the length of the reception chamber is adapted or variably adaptable to the human finger in a way that the elongate body is slipable over the human finger and flexibly guidable by means of movement of the finger of the finger. Advantageously, the inner circumference of the reception chamber is adapted to the outer circumference of the finger, so that the clearance is minimized or avoided. This allows for a highly precise guidance of the medical device by the finger.

According to the invention, the inner cross-sectional area of the reception chamber is variably adaptable to the human finger in a way that the elongate body lies substantially free of clearance against the human finger. This allows for a highly precise guidance of the medical device by the finger, since the finger is within the reception chamber closely encircled by the material of the reception chamber.

According to an advantageous embodiment of the invention, the length of the reception chamber is in a way adapted or variably adaptable to the human finger that the human finger is substantially completely insertable into the elongate body. This allows for the use of the whole finger, namely all phalanxes of the finger, for moving and guiding the medical device within the larynx. This is in particular important for persons having long airways to the trachea.

According to an advantageous embodiment of the invention, the elongate body is made of flexible material, wherein the elongate body comprises an area of increased stiffness which is arranged for insertion of the distal phalanx of the human finger. Hereby the guidability and preciseness of movement of the medical device can be further increased. The other areas of the elongate body can be manufactured with less stiffness, e.g. by thinner material or more elastic material.

According to an advantageous embodiment of the invention, the elongate body comprises in the longitudinal direction at least two sections. Herein, adjacent sections of the elongate body are connected to each other by an articular joint. The articular joint can be, for example, a hinge, a pivot or an articulation. For example, when the elongate body is made as a one-piece element, an articular joint can be manufactured by reducing the material thickness at a position where the articular joint shall be established.

Generally, the articular joints can be located below or above the position foreseen for the finger. According to an advantageous embodiment of the invention, one, more or all of the articular joints are located on a side of the reception chamber which is arrange for reception of the upper side of the finger. This allows for an improved ergonomic design of the medical device.

According to an advantageous embodiment of the invention, one, more or all of the articular joints are constructed as flexible articular section of the elongate body, which comprises a higher flexibility in the longitudinal direction of the elongate body than the other sections of the elongate body.

The image gathering device can be of any type, either an optical device or a non-optical device.

According to an advantageous embodiment of the invention, the image gathering device comprises a camera, a light guide or another kind of light guiding optical device. For example, it is possible to locate a miniaturised camera directly at the distal end of the elongate body. It is also possible to locate a camera separately from the medical device, and to guide the images through a light guide or other light guiding optical devices, like mirrors or prisms, from the distal end of the elongate body to the camera. In such case, the image gathering device comprises such light guiding elements. The image gathering device, e.g. the camera or the front end of the light guiding optical device, can be located in relation to the inserted finger beside the finger pad or finger nail. In such case any negative influence of the image gathering device on the tactile capabilities of the finger are minimized.

According to an advantageous embodiment of the invention, the image gathering device comprises a sonographic device, which is arranged for gathering images by means of ultrasound waves. The sonographic device can be located on or in the elongated body. It is also possible to guide a sonographic device through the one or more guiding elements along the medical device. In such case the sonographic device is a separate device.

According to an advantageous embodiment of the invention, the elongate body comprises a flushing channel, which has at least one emission opening for emitting a flushing medium. The at least one emission opening is located at the distal end of the elongate body and is adjusted in a way that emitted flushing medium is directed to the image gathering device. By use of the flushing medium, e.g. water, the image gathering device can be cleaned. This allows for maintaining a clear optical vision of the image gathering device during conductance of a laryngoscopy and/or an intubation.

According to an advantageous embodiment of the invention the elongate body comprises a first suction channel. The first suction channel comprises at least one first suction opening which is located at the distal end of the elongate body. The first suction channel allows for removing liquids and other debris in the area of the distal end of the elongate body.

According to an advantageous embodiment of the invention, the elongate body comprises a second suction channel. The second suction channel comprises at least one second suction opening, which is located at the distal end of the elongate body. The at least one second suction opening is adjusted in a way that flushing medium is extractable by suction. Advantageously the at least one second suction opening is located on the opposite side of the image gathering device in relation to the emission opening for emitting the flushing medium. This allows for easy and nearly complete removement of the flushing medium.

According to an advantageous embodiment of the invention an extension is located at the distal end of the elongate body, wherein the extension protrudes from the elongate body. In an advantageous embodiment, the extension protrudes in the longitudinal direction of the elongate body. The extension can be formed as a spatula. The extension can assist in guiding the medical device below the epiglottis in front of the larynx.

According to an advantageous embodiment of the invention, the medical device comprises a data interface for transmission of images gathered by the image gathering device to a display device, a computer and/or a data transmission unit for transmission of the images to a remote receiver. The transmission of images can be performed by a wired or wireless data transmission, in particular through Bluetooth or WLAN. The medical device can therefore comprise a data interface in the form a Bluetooth interface or a WLAN interface. The images can be transferred to a display device which displays the images. The images can alternatively or additionally be transmitted to a computer which stores and/or processed the images, e.g. by using of image processing algorithms. The display device and/or the computer can be part of the medical device, for example integrated into the elongate body, or can be separate parts, e.g. mountable to the arm of a user. Further, the images can be transmitted to a remote receiver which can be also connected to a display device and a computer. For example, the images can be displayed on a wall-mounted display in a medical operating room. Also, the images can be transmitted through a network to other persons, which allows getting assistance from remotely located persons during conductance of a laryngoscopy and/or an intubation.

According to an advantageous embodiment of the invention, the image gathering device is adjusted relative to the guiding element or the guiding elements for guiding the medical examination and/or intervention component in a way that a medical examination and/or intervention component inserted through the guiding elements appears substantially centrally in the images gathered by the image gathering device. This has the advantage that a user can easily correlate the images displayed on a display with the actual position of the medical examination and/or intervention component within the larynx and can more precisely further guide the medical examination and/or intervention component to the human or animal body, e.g. the trachea.

According to an advantageous embodiment of the invention, a distal guiding element for guiding the medical examination and/or intervention component is located at the distal end of the elongate body. The distal guiding element comprises an outlet port for the medical examination and/or intervention component. The distal guiding element is arranged for supporting the medical examination and/or intervention component at least in the dorsal and the palmar direction in relation to the inserted finger. Therefore, the medical examination and/or intervention component exits the elongate body at the outlet port. This has the advantage that a precise guiding of the medical examination and/or intervention component at the distal end of the elongate body is supported. The distal guiding element further limits the possible motion of the medical examination and/or intervention component to the left and right side. However, some clearance in the left and right side directions does not negatively influence the precise insertion of the medical examination and/or intervention component into the human or animal body, e.g. the trachea, but reduces the friction and therefore allows for an easy lateral movement of the medical examination and/or intervention component with only little manual effort by the user. Also, the medical device can be easily removed from the patient after insertion of the medical examination and/or intervention component into the orifice of the human or animal body, without unintentionally removing or dislocating the medical examination and/or intervention component. Again, the medical examination and/or intervention component can be e.g. an oral-tracheal tube or a biopsy needle.

According to an advantageous embodiment of the invention, the distal guiding element is located on the elongate body in the dorsal direction in relation to the inserted finger above the finger nail. This provides for an ergonomic operation of the medical device as well as for a precise guiding of the medical examination and/or intervention component through movement of the finger leading to a deformation of the elongate body.

According to an advantageous embodiment of the invention, the distal guiding element is arranged for guiding the medical examination and/or intervention component in the palmar direction upon exiting the outlet port, by means of a guiding ramp within the distal guiding element, in particular on the upper side of the inside of the distal guiding element. This makes it easier for the user to insert the medical examination and/or intervention component into the orifice of the human of animal body.

According to an advantageous embodiment of the invention, the guiding element or the guiding elements are located on the elongate body in the dorsal direction in relation to the inserted finger above the finger. This provides for an easy insertion of the medical examination and/or intervention component through the guiding elements as well as for a precise guiding of the medical examination and/or intervention component through movement of the finger leading to a deformation of the elongate body.

According to an advantageous embodiment of the invention, at least one guiding element is located on the elongate body on the left or ride side in relation to the inserted finger. It is particularly advantageous if a proximal guiding element located at the proximal end of the elongate body is located on the elongate body on the left or right side in relation to the inserted finger. By such a side guiding element the medical examination and/or intervention component is guided around the finger and on the one or other side of the finger, which allows for more operational space for the user in the vertical direction. This enables the complete introduction of the device into the orifice, e.g. the mouth, by turning the device during the introduction by 90 degrees around its longitudinal axis, even in patients with narrow mouth openings.

According to an advantageous embodiment of the invention, the elongate body comprises a thumb pressing area located at the proximal end of the elongate body between the inserted finger, which can be the index finger, and the thumb of the same hand. The thumb pressing area allows for a secure removement and/or position change of the medical device when operated within the larynx, by way of pressing the thumb on the thumb pressing area which will clamp the elongate body between the thumb and the index finger. The thumb pressing area shall have enough rigidity and stiffness to allow secure removement and/or position change of the medical device through such clamping.

According to an advantageous embodiment of the invention, the elongate body comprises a teeth protector which is formed as an extended portion of the elongate body at its proximal end on one or both dorsal sides. The teeth protector protects the inserted finger of the user against the teeth of the patient.

According to an advantageous embodiment of the invention, the medical device comprises a light source which is located at the distal end of the elongate body. The light source is arranged for emission of light. The light source can be a lamp or light emitting diode. Also, the light source can be a light guide or another kind of light guiding optical device, like an arrangement of mirrors or prisms, and an external lamp or light emitting diode. The light source has the advantage that the quality of the images gathered by the image gathering device can be improved since the area to be monitored by the image gathering device can be illuminated.

In the following the use and functions of the medical device of the invention are explained, whereby also further advantages and features of the medical device are described.

In case the medical device comprises the mentioned extension or spatula, the extension or spatula shall be positioned below the epiglottis. This has the advantage that an outlet opening for the tube is directed to the plica vocalis which increases the precision of the intubation. Further, the insertion of the tube is safer since the likelihood blocking through e.g. the epiglottis, the cartilagines arytaenoideae or the commissura posterior is reduced. The exit position of the distal guiding element is arranged in a way that by positioning the spatula below the epiglottis the tube exits directly below the spatula in front of the trachea. Therefore, an easy guiding of the tube into the trachea is facilitated. Even if the distance between the exit position of the tube and the trachea is increased, an easy orientation is possible since the tube always exits in the centre and appears therefore centrally in the images gathered by the image gathering device. This allows for an easy orientation within the larynx.

The tube can be inserted through the guiding elements without any lubricant, but however a lubricant can be used in addition. After insertion of the tube into the trachea the medical device can easily be removed from the patient by clamping the elongate body in the thumb pressing area between the thumb and the index finger inserted in the reception chamber, removing the medical device and the connecting the inserted tube section by means of a connector to another tube connected to an artificial respiration device.

The image gathering device can be built together with a light source. It is today possible to manufacture such a unit with a cross-section of only 4 mm. As an alternative, a light guide can be used, for example a polymer light guide. It is advantageous to use an image gathering device having a broad optical gathering area and a high image resolution.

The images can be displayed on one or more display units. A display unit can be mounted on the distal part of the arm of a user. It is also possible to use a display unit mounted on a separate frame. Display units of different size can be used, whereby a display unit adapted to be mounted on the arm of a user can have a size of 7×12 cm. Otherwise, display sizes of 10×15 cm are advantageous. It is advantageous that the display surface of the display unit is less or non-reflective for ambient light.

On the computer discrete images or sequences of images, like short movies, can be recorded and stored in an electronic documentation system. Also, a direct transmission of the images to a remote place is possible, which supports a distributed support by medical experts. The gathered images can also be used for training purposes, discussions and online-conferences. For this purpose, the medical device can be equipped or coupled to a microphone which allows for direct communication with remotely located other persons. Further, in addition to a microphone an additional camera can be foreseen, e.g. located on or near the display unit, for allowing a visual contact between the user of the medical device and remotely located persons.

A further optimisation is achieved by including an integrated flushing and suction system which serves to improve the visibility in all situations, also in case of conglomeration of blood, secretion or content from the stomach.

The flushing channel advantageously has a diameter of about one millimeter. The flushing channel as well as the first suction channel and the second suction channel can be connected through tubes via a Luer-Lock connector to a standard infusion system. Such a combined suction/flushing-drainage system allows for a permanent gathering of images with high quality without disturbance through liquids and/or debris within the larynx. The first suction channel and its suction opening can be located within the spatula. This allows for suction of liquids and debris in front of the elongate body which reduces the risk of an entry of gastric juice into the trachea.

Further, it is possible to use instead of a tube for artificial respiration of a person a specific tube for removing larger size debris particles, which might appear from the stomach.

The specific tube can be constructed like a surgical exhauster, having a cone-shaped tip and relatively thin outer wall with an inner diameter of about 10 mm. The specific tube comprises a cuff balloon which can be filled with air in order to seal the trachea. Below the cuff balloon can be several side openings, which assist in increasing the suction performance of the specific tube. Further, the side openings assist in providing a satisfactory suction performance if the front tip is blocked for any reason. The specific suction tube can be used in the same way as the oral-tracheal tube. Therefore, the same advantages apply as have been mentioned hereinbefore.

A further advantage of the medical device compared to conventional laryngoscopes is that the safety for a patient is increased by providing the possibility to guide the elongate body of the medical device through a combination of tactile sense and visual sense, which improves the orientation. Further, the guidance of the tube to the trachea is improved.

The medical device of the invention allows for guiding all integrated elements, including the integrated image gathering device, the outlet port for the tube and the first and second suction opening through the finger of the user, in particular through the finger tip of the user. This allows for a much more direct guidance and control of the medical device compared with conventional laryngoscopes having a handhold. The direct guidance allows for an intubation without any need for re-coordinating or re-thinking the three-dimensional situation during use, as it is required for all current conventional devices.

The use of the finger inserted into the medical device comprises the further advantage that the actual rigidity of the medical device can be directly influenced based upon the actual needs by the finger of the user through the finger muscles. Also, the finger provides for the possibility of a flexible adaptation to the airways of a user, depending upon the actual position within the airways.

Further, the medical device of the invention allows for a better tactile-optical controlled intubation of awake patients, after local anaesthesia of the mucosa, compared with the conventional method using a flexible bronchoscope or other video laryngoscopy systems. Therefore, with the medical device of the invention the possibilities of intubation of patients, where an increased risk of aspiration of gastric content is present, are improved.

Further, with the medical device of the invention other problems and potentially very dangerous situations that sometimes occur during conventional laryngoscopy can be avoided or at least decreased, like lip trauma, tooth damage, soar throat, damage in the airways, the trachea or other areas of the larynx, impacts on the circulation of the patient or stress caused through the intubation, and finally also an unnecessary loss of time in case of problematic intubations.

Experiments with the medical device were conducted with a simulator which has been prepared as so-called "patient with very difficult airway". Different test users tried to conduct an intubation upon the prepared simulator. A comparison was made with a conventional Macintosh laryngoscope and with optical and video laryngoscopes available on the market. With the conventional devices no successful intubation was possible. Compared with these devices, the medical device of the invention showed that all different test users were able to conduct a successful intubation within a timeframe of 14 to 43 seconds since starting the intubation process. No false intubation into the oesophagus happened.

The comparison tests were made in the following manner:

An airway training model "AirSim" was prepared by tying back the chin and stiffening the cervical spine in a way that the mentioned so-called "patient with very difficult airway" was present. We use this modified airway simulator together with other specially prepared phantom assemblies in our working group in workshops which we offer on different national congresses about anesthesia.

With the conventional Macintosh-type laryngoscope none of five test persons was able to visualise the vocal cord area of the modified airway simulator, which shows that by definition a very difficult airway was present. One test person was not able to visualise the laryngeal cover. All test persons tried for 15 to 39 seconds since introduction of the spatula to introduce the endotracheal tube in a "blind" manner which means that there was no view on the vocal cords (average time: 27.4 seconds, standard deviation: 10.5 seconds). All five test persons could not introduce the tube into the trachea, but conducted false intubation into the oesophagus.

With an optical laryngoscope, which shows in published studies conducted with airway simulators the best performance, two test persons were able to reach a complete view on the vocal cords. Two further test persons were able to reach a partial view on the vocal cords. One test person was not able to visualise the vocal cords. Where the visualisation was possible, the time required was between 7 and 71 seconds (average time: 27.4 seconds, standard deviation: 11 seconds). However, no test person was able to successfully conduct the intubation, because the endotracheal tube could not be passed through the larynx due to the very tight situation within the modified airway simulator. All five test persons discontinued their intubation activities after five unsuccessful trials.

With a video laryngoscope the test persons were able to visualise the lower entry of the larynx. No test person could visualise the vocal cords. One test person was able to only visualise the cover of the larynx. Another test person could even not visualise the cover of the larynx. It was not possible to push forward the tube in most cases, in some cases a false intubation into oesophagus happened due to lack of visualisation of the cover of the larynx. The intubation into the trachea was successful among those test persons who could visualise the entry of the larynx. Passing of the vocal cords with the endotracheal tube was possible in a time between 24 to 52 seconds (average time: 39.7 seconds, standard deviation 11.6 seconds) since insertion of the spatula.

In contrast to the aforementioned devices, with the device of the invention all five test persons were able to visualise the entry of the larynx and could conduct a successful intubation into the trachea. One test person was able to visualise the vocal cords completely, three test persons could visualise about the half of the vocal cords and one test person could visualise only the lower entry of the larynx. Passing the vocal cords with the endo-tracheal tube was possible in a time between 14 and 43 seconds (average time: 24.6 seconds, standard deviation: 11.5 seconds) since insertion of the elongate body into the modified airway simulator.

The invention is further described by means of examples using several drawings.

The drawings show:

FIG. 1—an upper part of a lying patient where the airways area is shown as sectional drawing, FIG. 2—a first embodiment of the medical device in a side view and FIG. 3—the first embodiment of the medical device in a front view and FIG. 4—the first embodiment of the medical device in a bottom view and FIG. 5—the first embodiment of the medical device in a top view and FIG. 6—a second embodiment of the medical device in a side view and FIG. 7—the second embodiment of the medical device with further details and FIG. 8—the second embodiment of the medical device in a front view.

In the drawing same numerals are used for same elements.

Figure 1:
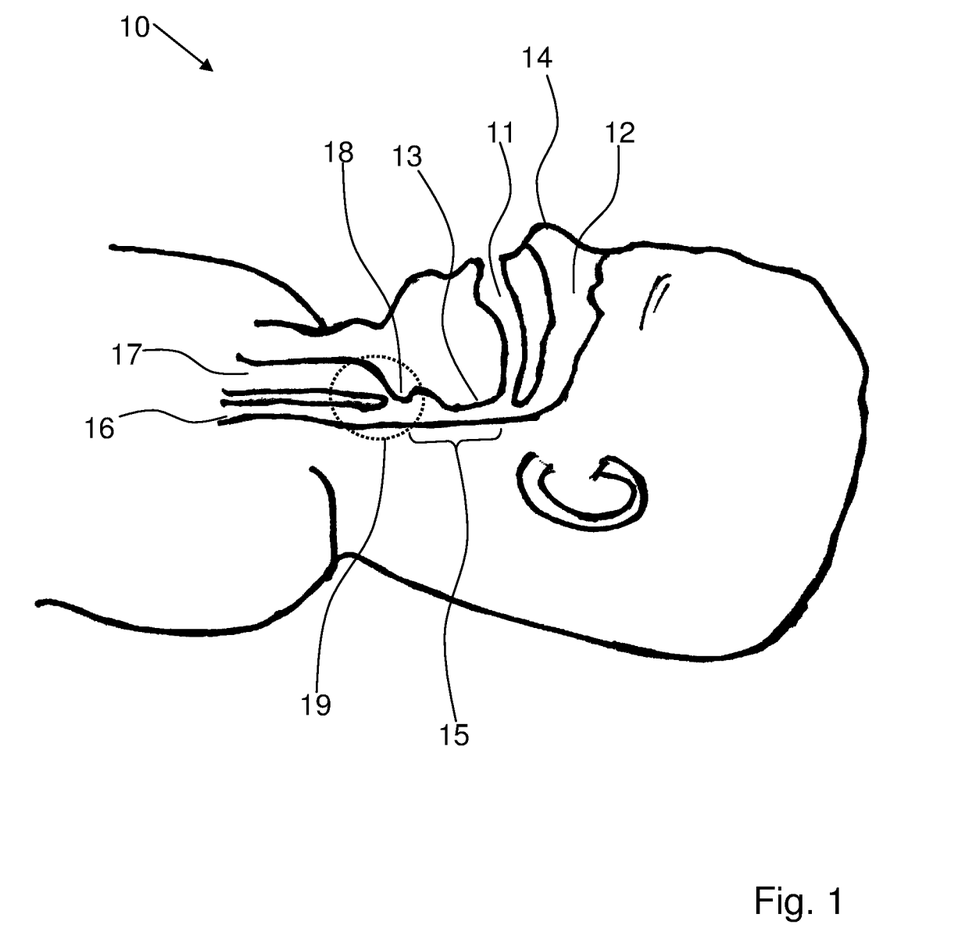

FIG. 1 shows the upper part of a lying person 10. Parts of the airway system of the person 10 are shown in a sectional view. FIG. 1 shows the oral cavity 11, the nasal cavity 12 in the area of the nose 14, the pharynx 15, the larynx 19, the epiglottis 18, the trachea 17 and the oesophagus 16. During a laryngoscopy and/or an intubation, a medical device, conventionally a laryngoscope, is inserted through the oral cavity 11 towards the tongue base 13 to enable the direct view to the larynx 15, the entry to the trachea 17. As it can be seen, the airways from the mouth to the trachea 17 are relatively narrow and angled. This makes a laryngoscopy and/or an intubation in some cases very difficult.

FIGS. 2 to 5 show a first embodiment of a medical device 1. In the following it is referred to these FIGS. 2 to 5.

The first embodiment of the medical device 1 comprises an elongate body 2 which is made as a hollow body comprising a reception chamber 8 in its interior. The reception chamber 8 is arranged for reception of a human finger 9. The elongate body can be formed, at least in the area of the reception chamber 8, similar like a tube or the finger part of a glove. The medical device comprises a distal end 3. The distal end 3 is on the front side of the elongate body 2 during the introduction into the pharynx 15 to reach the larynx 19. On the opposite side the elongate body 2 comprises a proximal end 4. The finger 9 is to be inserted into the reception chamber 8 from the proximal end 4. The medical device 1 is made of a flexible material which provides for enough flexibility to deform the medical device as needed during introduction into the pharynx 15 by means of the finger 9.

Figure 3:
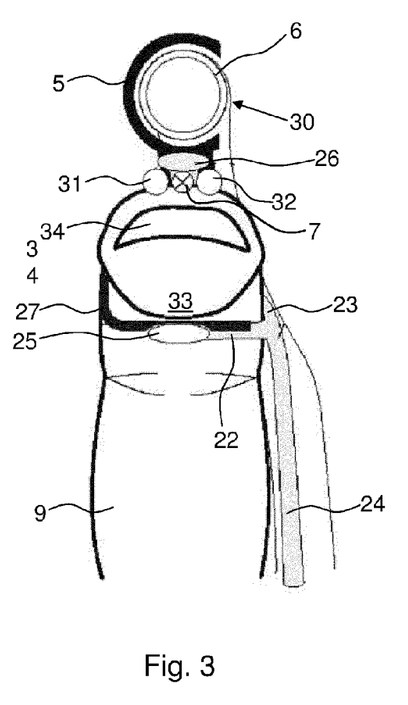
Figure 4:
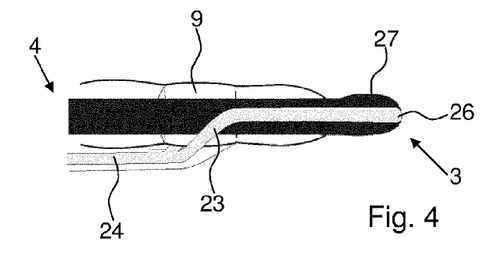

The medical device 1 comprises a guiding element 5 which is formed as a guiding channel, which serves for guiding an oral-tracheal tube 6. The guiding element 5 can be made as a one-piece channel or as sections of single guiding elements with intersections in between. As can be seen in FIG. 3, the guiding element 5 is not completely closed but comprises a side opening 30. After conducting the tube insertion process of the intubation, that is when the oral-tracheal tube is introduced into the trachea, the tube 6 can be removed from the guiding element 5 through the side opening 30. Then the medical device 1 can be removed from the person 10 while the tube 6 remains in the trachea 17.

The guiding element 5 comprises a distal guiding element 21, which comprises an outlet port 20 for the oral-tracheal tube 6. The distal guiding element 21 can be made integrally with other guiding elements 5 or as a separate guiding element. FIGS. 2 to 5 shows a distal guiding element 21 made integrally with the guiding element 5.

Figure 2:
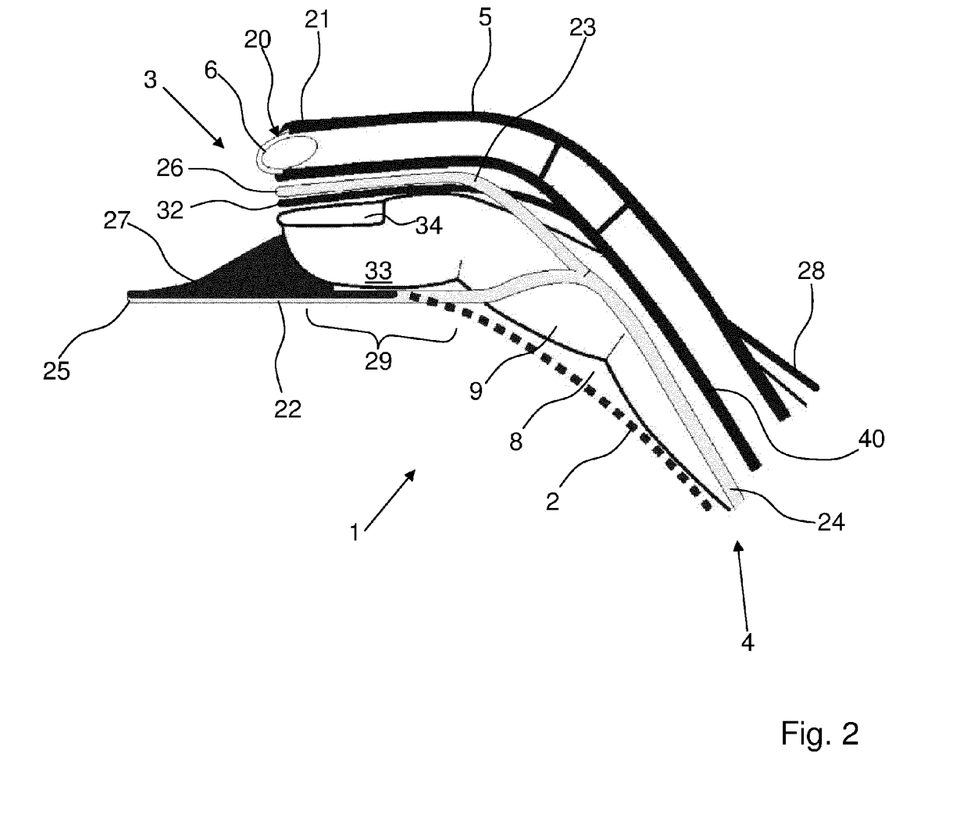
Figure 5:
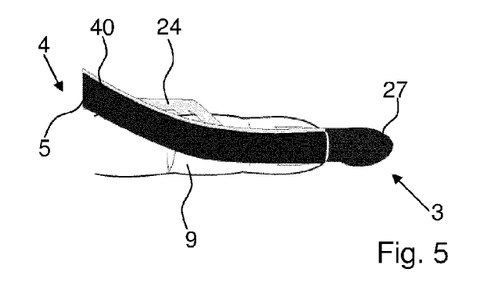

FIGS. 2 and 5 further show a proximal guiding element 40 which is in the shown embodiment also made integrally with the guiding element 5. The proximal guiding element 40 is located at the proximal end 4 of the elongate body 2 on the left side in relation to the inserted finger 9. The distal guiding element 21 is located above the inserted finger 9. This leads to a guidance of the tube 6 beginning on the left side of the finger 9, when the tube 6 is inserted into the proximal guiding element 40, to a position above the finger 9 when the tube 6 reaches the distal guiding element 21.

The medical device 1 further comprises a first suction channel 22 and a second suction channel 23. The first suction channel 22 comprises a first suction opening 25 which is located at the distal end 3, and more particularly at the end of an extension 27 which is formed as a spatula. The second suction channel 23 comprises a suction opening 26 which is located at the distal end 3. The first suction channel 22 and the second suction channel 23 are connected via a common tube 24 to a medical suction device.

In alternative embodiments, the extension 27 can be omitted or made shorter than shown in FIG. 2.

The medical device 1 further comprises an image gathering device 7 located at the distal end 3 between two emission openings 31, 32 for emitting a flushing medium. The image gathering device 7 comprises a miniaturised camera and a light emitting means for illuminating the area in front of the distal end 3 of the medical device. The image gathering device 7 is connected through an electrical cable, which is not shown in the figures, to an external electrical energy source and an image displaying device. On the left and right side of the image gathering device, the emission openings 31, 32 of a flushing channel 28 are located. Through the flushing channel 28 a flushing medium is transported to the emission openings 31, 32 and emitted through these openings.

In the area of the distal end 3 the elongate body 2 comprises an area 29 of increased stiffness. The increased stiffness provides for an improved force transmission from the finger 9 to lift the tongue base 13. This area 29 is arranged for insertion of the distal phalanx 33 of the human finger 9.

Figure 6:
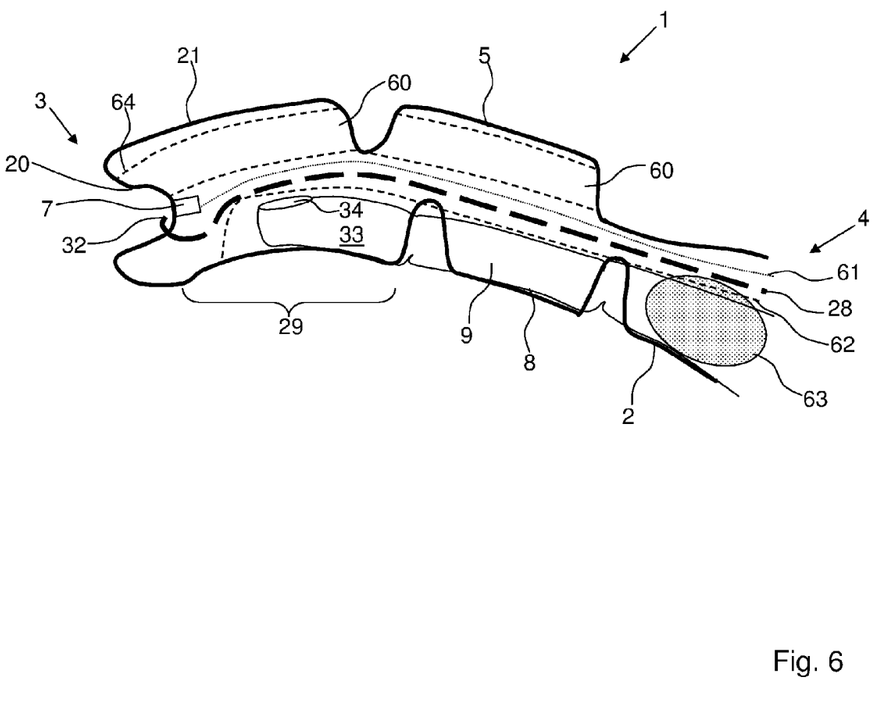
Figure 7:
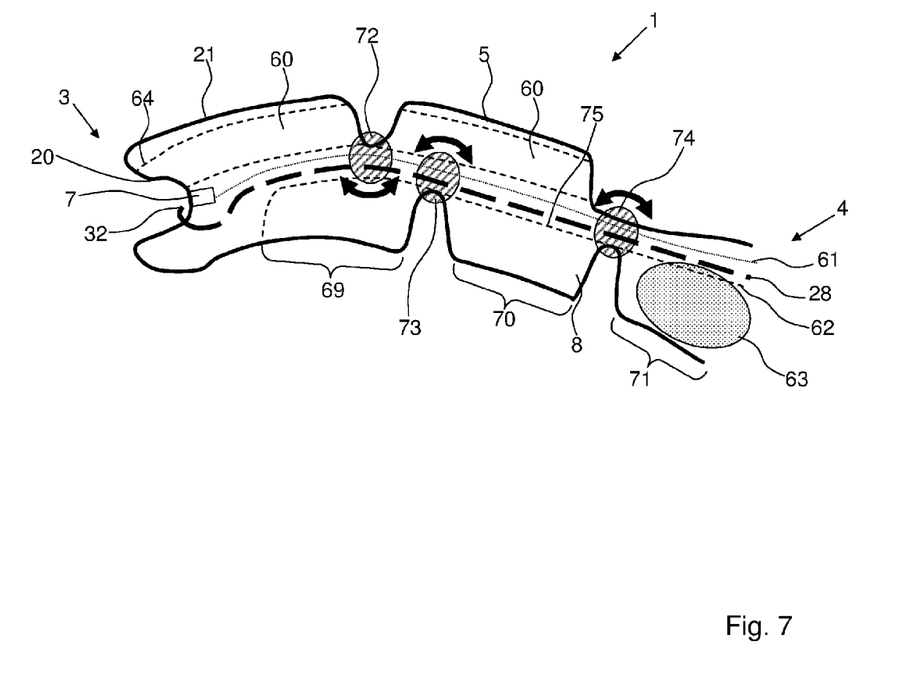
Figure 8:
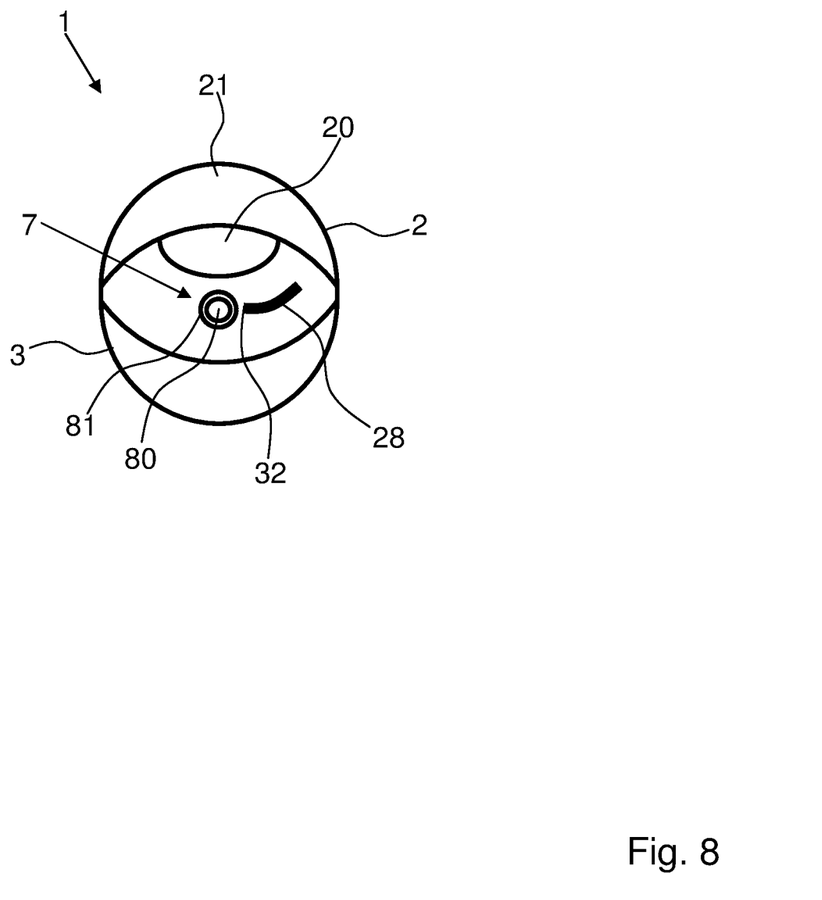

A second embodiment of the medical device 1 is shown in FIGS. 6 to 8 to which is referred hereinafter.

The medical device 1 comprises the elongate body 2. In the lower area of the elongate body 2 the reception chamber 8 is formed. In the upper area, the elongate body 2 comprises guiding elements 5, 21 for guiding an oral-tracheal tube. A guiding element located close to the distal end 3 is arranged as a distal guiding element 21 comprising the outlet port 20 for the oral-tracheal tube 6. The guiding elements 5, 21 form hollow chambers 60 through which the oral-tracheal tube 6 can be inserted.

Within the hollow chamber 60 of the distal guiding element 21 a certain upper area of the hollow chamber 60 close to the outlet port 20 is arranged as a guiding ramp 64. The guiding ramp 64 facilitates directing the tube 6 into the trachea 17 by supporting an outlet direction of the tube 6 in an optimum angle to reach the trachea.

Between the hollow chamber 60 and the reception chamber 8 the elongate body 2 comprises connection lines or tubes for the image gathering device 7, the first and second suction channels and the flushing channel. In FIGS. 6 to 8 only electrical connection lines 61 for connecting the image gathering device 7 to external equipment and the flushing channel 28 are shown. The connection lines or tubes can be integrated within the material of the elongate body 2.

As indicated in FIG. 7, the reception chamber 8 is split into several sections 69, 70, 71, whereby each of the sections 69, 70, 71 is arranged for reception of one phalanx of a human finger 9. Also, the hollow channel 60 guiding the oral-tracheal tube 6 is split into two sections, where an intersection is located between the guiding element 5 and the distal guiding element 21. Between adjacent sections each of sections 69, 70, 71 articular joints 73, 74 are located, which allow for a deformation of the elongate body 2 in the directions shown by the arrows close to the articular joints 73, 74. Further, another articular joint 72 is located between the guiding element 5 and the distal guiding element 21. The articular joint 72 allows for an easy deformation of the elongate body 2 in the direction of the arrow shown close to the articular joint 72.

As it can be seen, the articular joints 72, 73, 74 are located on a side 75 of the reception chamber 8 which is arranged for reception of the upper side of the finger, which means that the articular joints 72, 73, 74 are located above an inserted finger 9.

FIGS. 6 and 7 further show a thumb pressing area 63 located at the proximal end 4 of the elongate body 2. The thumb pressing area 63 allows for clamping the elongate body 2 between the thumb and the index finger inserted into the reception chamber 8.

FIG. 8 shows the elements mentioned before in a front view on the medical device 1. The image gathering device 7 is shown with further details, namely a miniaturised camera 80 and a light emission device 81 surrounding the camera 80. Further it is shown that an emission opening 32 of the flushing channel 28 is located close to the camera 80. The emission opening 32 is adjusted that emitted flushing medium is directed to the camera 80.

The invention claimed is:

1. A medical device for conducting a laryngoscopy and/or an intubation, the medical device comprising
   an elongate body which is designed for introduction into the pharynx, the elongate body comprising a distal end, which is on the front side of the elongate body during introduction into the pharynx, and a proximal end on the opposite side, wherein the elongate body is a hollow body comprising a reception chamber in its interior, which reception chamber is arranged for reception of a human finger,
   an oral-tracheal tube,
   one or more guiding elements, located on or in the elongate body, for guiding the oral-tracheal tube, wherein said oral-tracheal tube is removable from said one or more guiding elements after said introduction into the pharynx, and wherein said oral-tracheal tube is configured to remain in the pharynx after removal of the elongate body from the pharynx, and
   at least one image gathering device, which is arranged for gathering of images in front of the distal end of the elongate body, is arranged on or in the elongate body, wherein an outlet direction of the oral-tracheal tube from an outlet port of a distal guiding element is directed, in a side view of the medical device, towards the frontal gathering direction of the at least one image gathering device.

2. The medical device according to claim 1, wherein the inner cross-sectional area and/or the length of the reception chamber is adapted or variably adaptable to the human finger in a way that the elongate body is slipable over the human finger and flexibly guidable by means of movement of the finger in order to follow the movements of the finger.

3. The medical device according to claim 1, wherein the elongate body is made of flexible material, wherein the elongate body comprises an area of increased stiffness which is arranged for insertion of the distal phalanx of the human finger.

4. The medical device according to claim 1, wherein the elongate body comprises in the longitudinal direction at least two sections, wherein adjacent sections of the elongate body are connected to each other by an articular joint.

5. The medical device according to claim 4, wherein one, more or all of the articular joints are located on a side of the reception chamber which is arranged for reception of the upper side of the finger.

6. The medical device according to claim 4, wherein one, more or all of the articular joints are constructed as flexible articular section of the elongate body, which comprises a higher flexibility in the longitudinal direction of the elongate body than the other sections of the elongate body.

7. The medical device according to claim 1, wherein the image gathering device comprises a camera, a light guide or another kind of light guiding optical device.

8. The medical device according to claim 1, wherein the image gathering device comprises a miniaturised camera, which is located at the distal end of the elongate body.

9. The medical device according to claim 1, wherein the elongate body comprises a flushing channel, which has at least one emission opening for emitting a flushing medium, wherein the at least one emission opening is located at the distal end of the elongate body and is adjusted in a way that emitted flushing medium is directed to the image gathering device.

10. The medical device according to claim 1, wherein the elongate body comprises a first suction channel, wherein the first suction channel comprises at least one first suction opening which is located at the distal end of the elongate body.

11. The medical device according to claim 10, wherein the elongate body comprises a second suction channel, wherein the second suction channel comprises at least one second suction opening, which is located at the distal end of the elongate body, wherein the at least one second suction opening is adjusted in a way that flushing medium extractable by suction.

12. The medical device according to claim 1, wherein the medical device comprises a data interface for transmission of images gathered by the image gathering device to a display device, a computer and/or data transmission unit for transmission of the images to a remote receiver.

13. The medical device according to claim 1, wherein the image gathering device is adjusted relative to the guiding element or the guiding elements for guiding the oral-tracheal tube in a way that an oral-tracheal tube inserted through the guiding elements appears substantially centrally in the images gathered by the image gathering device.

14. The medical device according to claim 1, wherein a distal guiding element for guiding the oral-tracheal tube is located at the distal end of the elongate body, wherein the distal guiding element comprises an outlet port for the oral-tracheal tube, wherein the distal guiding element is arranged for supporting the oral-tracheal tube at least in a dorsal and a palmar direction.

15. The medical device according to claim 1, wherein a distal guiding element for guiding the oral-tracheal tube is located at the distal end of the elongate body, wherein the distal guiding element comprises an outlet port for the oral-tracheal tube, wherein the distal guiding element is located on the elongate body in a dorsal direction.

16. The medical device according to claim 1, wherein said one or more guiding elements include a side opening for permitting removal of said oral-tracheal tube.

* * * * *